United States Patent
Ruyters et al.

(10) Patent No.: US 11,454,688 B2
(45) Date of Patent: Sep. 27, 2022

(54) SYSTEM AND METHOD FOR PROVIDING AT LEAST ONE PARAMETER FOR A MAGNETIC RESONANCE SCAN

(71) Applicant: Siemens Healthcare GmbH, Erlangen (DE)

(72) Inventors: Gudrun Ruyters, Erlangen (DE); Johann Sukkau, Herzogenaurach (DE); Michael Wullenweber, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 11 days.

(21) Appl. No.: 17/024,977

(22) Filed: Sep. 18, 2020

(65) Prior Publication Data

US 2021/0088613 A1 Mar. 25, 2021

(30) Foreign Application Priority Data

Sep. 23, 2019 (EP) .................................... 19198969

(51) Int. Cl.
| | |
|---|---|
| *G01R 33/48* | (2006.01) |
| *A61B 5/055* | (2006.01) |
| *G01R 33/54* | (2006.01) |
| *G01R 33/56* | (2006.01) |
| *G06T 7/00* | (2017.01) |

(52) U.S. Cl.
CPC .......... *G01R 33/4828* (2013.01); *A61B 5/055* (2013.01); *G01R 33/546* (2013.01); *G01R 33/5608* (2013.01); *G06T 7/0012* (2013.01); *G06T 2207/10088* (2013.01); *G06T 2207/20081* (2013.01)

(58) Field of Classification Search
CPC .............. G01R 33/4828; G01R 33/546; G01R 33/5608; A61B 5/055; G06T 7/0012
See application file for complete search history.

(56) References Cited

U.S. PATENT DOCUMENTS

| | | | |
|---|---|---|---|
| 4,899,109 A * | 2/1990 | Tropp | G01R 33/3875 324/319 |
| 9,662,037 B2 * | 5/2017 | Takahashi | A61B 5/055 |
| 2012/0119740 A1 * | 5/2012 | Takahashi | G01R 33/48 324/309 |
| 2015/0226822 A1 | 8/2015 | Campagna | |

(Continued)

OTHER PUBLICATIONS

European Search Report for European Application No. 19198969.8-1010 dated Apr. 7, 2020.

(Continued)

*Primary Examiner* — Dixomara Vargas
(74) *Attorney, Agent, or Firm* — Lempia Summerfield Katz LLC

(57) ABSTRACT

A method and a system for providing parameters of a resonance frequency spectrum of a magnetic resonance scan. The system includes: an input interface for receiving a resonance frequency spectrum of a magnetic resonance scan and a computing device configured to implement a trained machine learning algorithm. The trained machine learning algorithm is trained to receive the resonance frequency spectrum received by the input interface as its input and to generate as its output a set of parameters of the resonance frequency spectrum. The system further includes an output interface configured to output the generated set of parameters.

20 Claims, 3 Drawing Sheets

(56) References Cited

U.S. PATENT DOCUMENTS

| | | | | |
|---|---|---|---|---|
| 2016/0161580 | A1* | 6/2016 | Shirai | G01R 33/543 |
| | | | | 324/322 |
| 2016/0274156 | A1* | 9/2016 | Niederloehner | G01R 33/583 |
| 2016/0291108 | A1* | 10/2016 | Niederloehner | G01R 33/4828 |
| 2017/0261586 | A1* | 9/2017 | Carinci | G01R 33/5607 |
| 2018/0217216 | A1* | 8/2018 | Suh | G01R 33/543 |
| 2018/0252786 | A1* | 9/2018 | Sukkau | G01R 33/56563 |
| 2018/0268546 | A1* | 9/2018 | Sun | G01R 33/48 |
| 2018/0292495 | A1* | 10/2018 | Sun | G01R 33/5673 |
| 2019/0011516 | A1* | 1/2019 | Sun | G01R 33/4838 |
| 2021/0181284 | A1* | 6/2021 | Sukkau | G16H 10/60 |

OTHER PUBLICATIONS

Goldfarb, James W., Jason Craft, and J. Jane Cao. "Water—fat separation and parameter mapping in cardiac MRI via deep learning with a convolutional neural network." Journal of Magnetic Resonance Imaging 50.2 (2019): 655-665.

Saudek, Erik, et al. "Analysis of Human Brain NMR Spectra in Vivo Using Artificial Neural Networks." International Conference on Artificial Neural Networks. Springer, Berlin, Heidelberg, 2008. pp. 1-10.

Yi, Ling, and Jinliang Ding. "NMR principle analysis based object detection for intelligent measurement of crude oil moisture content." 2019 12th Asian Control Conference (ASCC). IEEE, 2019. pp. 1-6.

* cited by examiner

SYSTEM AND METHOD FOR PROVIDING AT LEAST ONE PARAMETER FOR A MAGNETIC RESONANCE SCAN

CROSS REFERENCE TO RELATED APPLICATIONS

This application claims the benefit of EP 19198969.8 filed on Sep. 23, 2019, which is hereby incorporated by reference in its entirety.

FIELD

Embodiments relate to a system and a method for providing at least one parameter for a magnetic resonance scan of a patient.

BACKGROUND

In magnetic resonance, MR, scans (i.e. image acquisitions), the nuclear spins of hydrogen atoms are resonantly excited by radio frequency pulses. The resonance frequency of each spin is proportional to the magnetic field B0 at the location of the nucleus of the hydrogen atoms. The terms "frequency" and "B0" are sometimes used as synonyms.

In any MR scan, the local B0 field may vary for a number of reasons. For example, the magnetic field strength may drift, e.g. due to temperature changes in the magnet cooling shields that may lead to global frequency shifts. Also, the susceptibility of biological matter in the patient's body and its boundaries may lead to local frequency shifts, generally addressed by shimming. Shimming is a process, by which the main magnetic field is made more homogeneous.

Microscopic frequency shifts may also be caused as a result of the chemical bonds of the hydrogen atom, for example in fat or water molecules. The chemical shifts are known in parts per million, ppm.

In order to achieve best possible contrast and signal-to-noise-ratio, SNR, and to successfully employ techniques such as fat or water saturation, the resonance frequencies of the hydrogen atoms within the field of view of each MR scan have to be precisely known. A frequency adjustment measurement is conducted for each MR scan using a specialized sequence. The result is a spectrum of signal intensities per frequency inside the field of view of the MR scanning device. The spectra may be designated as resonance frequency spectra, RFS.

These resonance frequency spectra may include peaks that correspond to resonance frequency maxima for different substances such as fat or water. FIG. 6 depicts a schematic resonance frequency spectrum 1 with a distinct peak 2 for resonance frequency of (body) fat and a distinct second peak 3 for the resonance frequency of water. The horizontal axis depicts frequency values as deviations from a currently set frequency value for the resonance frequency of water, and the vertical axis signal strength in arbitrary units. Current algorithms determine the peaks (for water: dashed lines) by adjusting Lorentzian functions to the resonance frequency spectrum, RFS, and use an optimization to create a best fit. In this way, a fitting curve 4 for a resonance frequency spectrum, RFS, as shown in FIG. 5 is generated automatically.

However, in other cases, as depicted in FIG. 7, the measured resonance frequency spectrum 5 may be more complicated so that the fitting curve 6 generated by the prior art algorithms often fails to capture the details of the resonance frequency spectrum, RFS.

SUMMARY

The scope of the present disclosure is defined solely by the appended claims and is not affected to any degree by the statements within this summary. The present embodiments may obviate one or more of the drawbacks or limitations in the related art.

Embodiments provide improved systems and methods for providing at least a water resonance frequency value based on a measured resonance frequency spectrum.

Embodiments provide according to a first aspect a system for providing at least one parameter for a magnetic resonance, MR, scan, including an input interface for receiving an RFS of an MR scan, a computing device configured to implement a trained machine learning algorithm, MLA, and an output interface. The trained MLA is trained to receive the RFS received by the input interface as its input and to generate as its output at least one parameter, the at least one parameter including at least a water resonance frequency value. The output interface is configured for outputting at least the generated water resonance frequency value.

The at least one parameter may be a parameter of a fitting curve to the resonance frequency spectrum, RFS, for example a Lorentzian fitting curve, but may also include or include other types of fits such as a polynomial fit, a Gaussian fit and/or the like.

It is possible that the output includes only of the water resonance frequency value, in that case only this value as a single parameter is output by the machine learning algorithm and the output interface. Whenever a "set of parameters" or a "parameter set" is mentioned herein, this is done for the sake of lucidity in the description, and shall be understood to include the case that the parameter set include of only a single parameter, i.e. the water resonance frequency value.

The water resonance frequency value may be the position of a Lorentzian fitting curve (or any other type of fitting curve) to a local maximum within the resonance frequency spectrum. In some cases, e.g. due to inhomogeneity of a magnetic field of the MR scanning device, the actual resonance frequency spectrum includes more than one, e.g. two, peaks that are related to water. In that case, the water resonance frequency value output by the machine learning algorithm may not correspond to one single peak in the resonance frequency spectrum but may, for example, lie in between.

The water resonance frequency value may either be an absolute value describing the water resonance frequency, or it may be an offset value describing an offset of the determined water resonance frequency with respect to a reference frequency. The reference frequency may be fixed, or it may be set to a currently set resonance frequency of an MR scanning device. For example, in FIG. 1 and FIG. 2 the horizontal axes depict such offset values.

The output may include additional parameters of the resonance frequency spectrum. The parameters are "of" the resonance frequency spectrum in that the parameters describe properties of the resonance frequency spectrum.

Instead of a fixed algorithm, a machine learning algorithm is configured to generate the set of parameters of the resonance frequency spectrum, RFS, that may be continuously improved and updated. In this way, over time, even resonance frequency spectra that are ordinarily exceedingly difficult to parameterize by fixed algorithms may be learned by the machine learning algorithm.

The input interface and/or the output interface may be configured in hardware and/or software. The input interface and/or the output interface may each include one or more different communication channels using one or more different communication protocols (e.g. HTTP). Each of the input interface and/or the output interface may be configured to connect to a cable-bound data connection and/or to a wireless data connection such as Bluetooth, Zigbee, Wi-Fi and so on. The input interface and/or the output interface may also be configured to connect to Ethernet networks.

The computing device may be configured as any device for computing. For example, the computing device may include at least one data processing (or: calculating) unit such as at least one central processing unit, CPU, and/or at least one graphics processing unit, GPU, and/or at least one field-programmable gate array, FPTA, and/or at least one application-specific integrated circuit, ASIC, and/or any combination of the foregoing. The computing device may include a working memory operatively coupled to the at least one processing unit and/or a non-transitory memory operatively connected to the at least one processing unit and/or the working memory.

The computing device may be partially or completely configured as a remote device, for example as a cloud computing platform. In an embodiment, the parameters are a plurality (of at least two) parameters and further include, for at least one local maximum of the resonance frequency spectrum: a position of the local maximum, a full width at half maximum, FWHM, of the local maximum, and/or a height (or: value) of the local maximum.

The set of parameters may be used for debugging, for displaying a fitting curve based on these parameters to a user via a display device so that the user may confirm/correct the fitting curve and/or the like.

When the set of parameters is intended to correspond to more than one local maximum, each of the quantities may be included for each of the local maxima. All of the quantities may be provided for all of the local maxima, for which parameters are to be generated.

In an embodiment, the parameters indicate, for the at least one local maximum of the fitting curve to the resonance frequency spectrum, to which type of substance or tissue the at least one local maximum corresponds. For example, the set of parameters may indicate for each of: water, fat, and/or silicon a corresponding local maximum of the fitting curve to the resonance frequency spectrum.

The set of parameters indicates for each of the substances a corresponding local maximum. For each of the local maxima the three quantities position, full width at half maximum and height may be generated. Thus, in one embodiment, position, full width at half maximum and height of the maximums for water, fat and silicon are generated by the machine learning algorithms, so that in total nine parameter values are generated. Accordingly, when the machine learning algorithm is an artificial neural network, an output layer of the artificial neural network may include nine output nodes, each of which generates one of the parameters.

Such a set of parameters may be logged and/or may be used to display the fitting curve to the resonance frequency spectrum to a user in order to support the user in confirming/correcting the fitting curve.

In another embodiment, position, full width at half maximum and height of the local maxima for water and fat are generated so that in total six parameters are generated. Correspondingly, an output layer of an artificial neural network as a machine learning algorithm may include six output nodes.

In certain embodiments, the machine learning algorithm is a feed-forward artificial neural network, ANN, and/or a deep neural network, i.e. an artificial neural network including at least one hidden layer. The feed-forward artificial neural network may be a fully connected artificial neural network including, for example, from four to ten hidden layers, more preferably from four to six hidden layers. Each of the hidden layers may include from ten to one thousand neurons, preferably from fifty to two hundred neurons. In other embodiments, the artificial neural network may include at least one convolutional neural sub-network or may be a convolutional neural network.

Conventionally, a drop-out function is often applied during the training of artificial neural networks in order to prevent overfitting. However, even in the already trained artificial neural network, i.e. in the inference phase, at least one additional dropout layer may be provided. During inference, a predefined number (or even randomized) of randomly chosen nodes may be deactivated ("dropped out") for each processing of a particular resonance frequency spectrum in order to analyze the reliability of the generated output of the artificial neural network, ANN, for the resonance frequency spectrum, RFS.

Generally, if for a large number of dropout configurations of the dropout layer (i.e. for many different combinations of dropped-out, or deactivated, nodes of the dropout layer) the generated at least one parameter varies only to a small degree, this indicates a high reliability of the generated at least one parameter. This is because the relative independence of the nodes active during inference in the dropout layer(s) means that the decision basis for the generation of the at least one parameter is broad, i.e. based on many "paths" through the artificial neural network, ANN. If, for each combination of drop-out nodes the generated at least one parameter is vastly different, this indicates a low reliability of the generated at least one parameter, because the output of the machine learning algorithm then seems to be strongly dependent on individual nodes. Thresholds may be defined that categorize different results of the drop-out analysis into different reliability categories.

In certain embodiments, the system further includes a user interface, for example a touch-screen interface implementing a graphical user interface, a computer monitor in combination with a keyboard and/or a mouse, a speech-controlled user interface and/or the like. The user interface may be configured to obtain, at least in a revision mode of the system, revision information by a user. The user may put the system into the revision mode, or the system may permanently be in the revision mode.

The revision information indicates a resonance frequency spectrum, RFS, for which the trained machine learning algorithm, MLA, has generated the parameter set as well as indicate a confirmation of at least one parameter of the at least one generated parameter and/or a correction to at least one parameter of the at least one generated parameter. The revision information may include at least a confirmation or correction of the water resonance frequency value.

A confirmation of at least one parameter may signify that the user has found the at least one parameter to be accurate according to their criteria. A correction to at least one parameter may include a corrected value for the at least one parameter. In an embodiment, for example, in the revision mode the user is provided via the user interface with all of the generated parameters as well as with a graphical indication of the resonance frequency spectrum. The user may then, for each parameter, indicate whether the parameter is correct (confirmation) or instead indicate a corrected value (correction) for each parameter.

In the case that at least one correction has been made, the corrected parameter set (i.e. the corrected at least one parameter) is output by the output interface. In case that all of the parameters have been confirmed with a confirmation, the originally generated parameter (set) may be output for further processing. For example, the parameter (set) may be output to an MRI scanning device. For example, the generated parameter (set) may be part of a control signal generated by the output interface. The control signal is configured to control an MR scanning device (or: MR imaging device, MRI device) based on the generated parameter set. The corrected or confirmed water resonance frequency value may be part of a control signal, or the control signal to control the MR scanning device may be based on the generated water resonance frequency value.

In certain embodiments, the machine learning algorithm, MLA, further receives as its input, together with the resonance frequency spectrum, RFS, at least one piece of patient information about the patient from which the resonance frequency spectrum, RFS, was taken. For example, the at least one piece of patient information may include information about at least one of: a weight of the patient, a height of the patient, an age of the patient, a sex of the patient, and/or a body region of the patient from which the resonance frequency spectrum was taken.

The machine learning algorithm may be trained more specifically not only based on the resonance frequency spectra, but also on the specific circumstances or boundary conditions under which the respective resonance frequency spectrum has been taken, i.e. generated.

In certain embodiments, the machine learning algorithm, MLA, includes at least one drop-out layer. The computing device may be further configured to determine a reliability of the generated at least one parameter by at least one configuration of the at least one drop-out layer. An output of the machine learning algorithm, MLA, may be generated for each of a plurality of (for example, randomized) configurations of the at least one drop-out layer regarding the drop-out nodes of the drop-out layer, and the reliability is determined based on an analysis of the results for the plurality of configurations. The computing device may implement a reliability determination module for determining the reliability in this way, i.e. to determine a reliability metric.

The output interface may be further configured to output the determined reliability metric. The system also provides a measure for the reliability of its output. This is in particular important given current endeavors to provide understandable and reproducible results from machine learning algorithms.

According to an embodiment, a computer-implemented method for providing at least one parameter of a resonance frequency spectrum, RFS, of a magnetic resonance, MR, scan is provided. The method includes receiving an RFS of an MR scan; applying a trained machine learning algorithm, MLA, to the received RFS, whereby as its output at least one parameter is generated, the at least one parameter including (or consisting of) at least a water resonance frequency value; and outputting at least the water resonance frequency value generated by the trained MLA based at least on the inputted RFS.

In certain embodiments, the machine learning algorithm used in the method includes at least one drop-out layer, and the method includes a step of determining a reliability of the generated at least one parameter based on at least one configuration of the at least one drop-out layer, for example as has been described above. In addition, the method may include a step of outputting the determined reliability (or: reliability metric, specifically a reliability value).

According to an embodiment, a computer-implemented method for training a machine learning algorithm, MLA, for use in the system is provided. The machine learning algorithm, MLA, is trained with labeled resonance frequency spectra. The resonance frequency spectra may be labeled with the same at least one parameter that the machine learning algorithm is configured to generate based on the resonance frequency spectrum. The resonance frequency spectra are thus labelled with a respective water resonance frequency value ground truth. Some or even all of the labeled resonance frequency spectra may stem from one or more user interfaces, by which users have, in revision mode of the system, confirmed and/or corrected previously generated parameter(s).

In embodiments of the system, a pre-trained machine learning algorithm is provided to users and is then further refined (i.e. additionally trained) based on the revision information provided, via the user interface, by the users.

In certain embodiments, the machine learning algorithm, MLA, is additionally trained with the at least one piece of patient information about each of the patients from which the labeled resonance frequency spectra were taken. The machine learning algorithm is configured to also receive in the inference phase, for example, during the method for providing at least one parameter of the resonance frequency spectrum, RFS, the same at least one piece of patient information and to generate the at least one parameter also based thereon. For example, the at least one piece of patient information may include information about a weight of the patient, a height of the patient and/or a body region of the patient, from which the resonance frequency spectrum was taken.

In certain embodiments, a machine learning algorithm, MLA, is further trained using revision information received by users.

According to an embodiment, a computer program product is provided including executable program code configured to, when executed by a computing device, to perform any embodiment described herein.

According to an embodiment, a non-transitory, computer-readable data storage medium is provided, that includes program code configured to, when executed by a computing device, executes the method according to an embodiment. The data storage medium may be, for example, a USB stick, a CD ROM, a DVD ROM, a Blue-Ray Disc, a hard drive, a solid-state drive, and/or the like.

According to an embodiment, a data stream is provided, that includes program code (or which is configured to generate program code), configured to, when executed by a computing device, perform the method according to any embodiment. The data stream may, for example, be provided by a server and be downloaded by a client or a user terminal or by a personal computer or a laptop.

Additional advantageous variants, refinements, embodiments, and aspects of the invention will become more obvious in connection with the following description with reference to the drawings.

DETAILED DESCRIPTION

Figure 1:
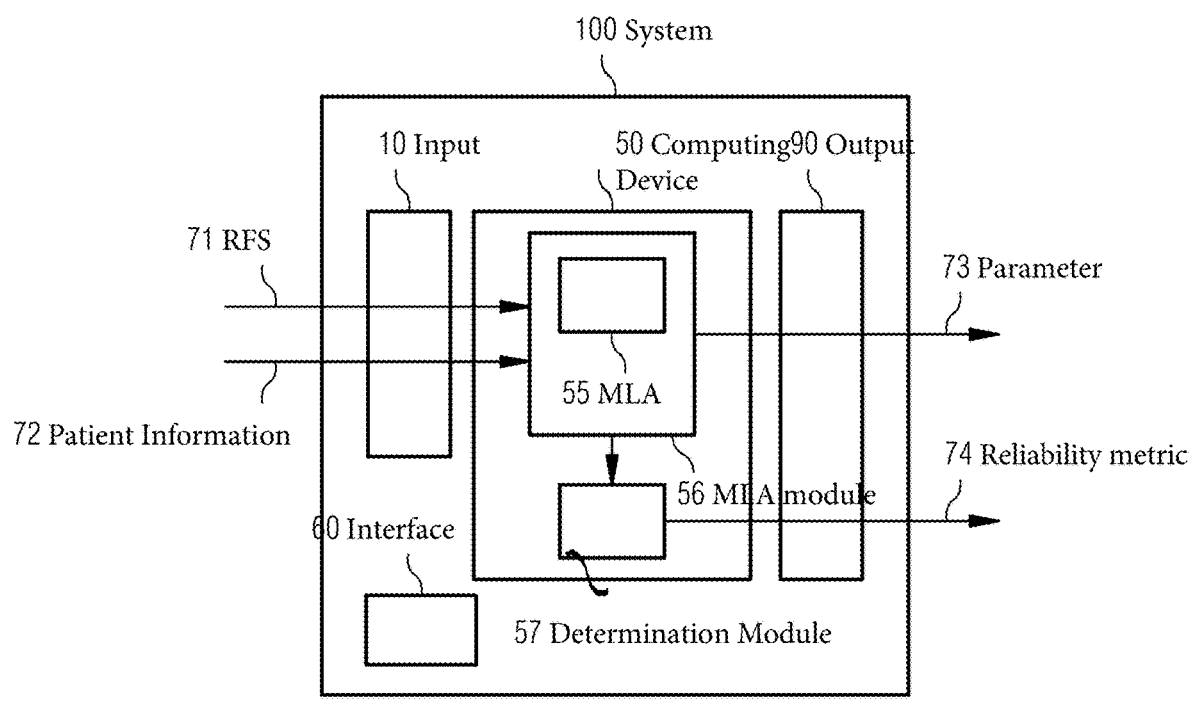
FIG. 1 depicts a schematic block diagram illustrating a system according to an embodiment.

FIG. 1 depicts a schematic block diagram illustrating a system 100 according to an embodiment. FIG. 1 depicts a schematic block diagram of a system 100 for providing at least one parameter 73 of a resonance frequency spectrum, RFS, 71 of a magnetic resonance, MR, scan. The system 100 includes an input interface 10 for receiving a resonance frequency spectrum, RFS, of a magnetic resonance, MR, scan. The system 100 also includes a computing device 50 configured to implement a trained machine learning algorithm, MLA 55. The computing device 50 may include a dedicated machine learning algorithm, MLA, module 56 configured to implement the trained MLA 55. The MLA module 56 may in particular be configured as software run by the computing device 50. The software may be stored in a non-transitory data storage of the computing device 50 and may be run in a working memory of the computing device 50.

The trained MLA 55 is trained to receive the RFS 71 received by the input interface 10 as its input and to generate, as its output, at least one parameter 73 of (or: for) the RFS 71. The at least one parameter 73 includes a water resonance frequency value.

The system 100 further includes an output interface 90 for outputting the generated at least one parameter. The generated at least one parameter 73 may be output e.g. to an external database for storing therein, for example together with the corresponding RFS. In an embodiment, a plurality of parameters 73 is generated, i.e. a set of parameters 73. However, in certain embodiments, only the water resonance frequency value is generated and output by the output interface 90.

As water, fat and silicon are the most important substances of a human body that react to a MR scan, the set of parameters 73 may indicate corresponding local maxima within fitting curves (e.g. Lorentzian, Gaussian etc. fits) to the resonance frequency spectra, RFS, for water, and for fat and/or for silicon. For some applications, the set of parameters 73 may merely indicate the location of the indicated local maxima.

The position of each indicated local maximum, the full width at half maximum, FWHM, of each indicated local maximum and the height of each indicated local maximum may be included within the set of parameters 73.

In an embodiment, the set of parameters 73 includes of six parameters, that are position, full width at half maximum, FWHM, and height for each of water and fat. The set of parameters may include nine parameters, that are the position, the full width at half maximum, FWHM, and the height for local maxima corresponding to water, fat, and silicon.

The trained machine learning algorithm, MLA, 55 may be a feed-forward artificial neural network, ANN, that is trained to receive as its input at least a resonance frequency spectrum, RFS, 71 and to generate based at least thereon the at least one parameter 73, including at least the water resonance frequency value.

When the machine learning algorithm, MLA, 55 is configured as an artificial neural network, ANN, the artificial neural network, ANN, may include be a feed-forward artificial neural network, ANN and/or a deep neural network, i.e. an artificial neural network, ANN, including at least one hidden layer. The feed-forward artificial neural network may be a fully connected artificial neural network including, for example, from four to ten hidden layers or from four to six hidden layers. Each of the hidden layers may include from ten to one thousand neurons, for example from fifty to two hundred neurons. In other embodiments, the artificial neural network may include at least one convolutional neural sub-network or may be a convolutional neural network.

The machine learning algorithm, MLA, 55 may further be configured to receive as its input at least one piece of patient information 72 about a patient from which the resonance frequency spectrum, RFS, 71 input into the machine learning algorithm, MLA, 55 has been taken. For example, the machine learning algorithm, MLA, 55 may further be trained and configured to receive information about a weight of the patient, a height of the patient and/or a body region of the patient from which the resonance frequency spectrum, RFS, 71 has been taken.

In case that the artificial neural network, ANN, has been trained to receive at least one piece of patient information and in the further case that for a specific resonance frequency spectrum, RFS, during the inference phase the piece of patient information is not available, an average or standardized value for the patient information may be used in order to allow the artificial neural network, ANN, 55 to generate the desired at least one parameter 73.

The system 100 may also be configured to receive, via the input interface 10, together with the resonance frequency spectrum, RFS, 71 the at least one piece of patient information 72 and/or a patient identifier information, that indicates, preferably in a coded way, the corresponding patient. In cases in which only the patient identifier information, but not the at least one piece of patient information 72 is provided, the at least one piece of patient information needed may be automatically requested by the system 100. For example, the output interface 90 could be configured to request the necessary information from a patient database based on the patient identifier information. When at least part of the system 100, on particular the computing device 50, is at least partially configured as a cloud computing device, it is preferred that any information that relates to particular patients such as patient identifier information, is only transmitted in an encrypted way.

When the machine learning algorithm, MLA, 55 is configured as an artificial neural network, ANN, the artificial neural network, ANN, may include at least one drop-out layer. The computing device 50 may be further configured to determine a reliability metric 74 for the generated set of parameters by at least one configuration of the at least one drop-out layer. Preferably, the system 100 is configured such that an output (i.e. the at least one parameter 73) of the machine learning algorithm, MLA, 55 is generated for each of a plurality of (preferably randomized) configurations of the at least one drop-out layer regarding the drop-out nodes of the drop-out layer, and the reliability metric 74 is determined based on an analysis of the results for the plurality of configurations.

The computing device 50 may implement a reliability determination module 57 for determining (or: calculating, or generating) the reliability metric 74. For example, the reliability determination module 57 may be configured to determine a difference metric for the different parameters 73 (i.e. outputs) generated for the same input of the artificial neural network, 55 but with different configurations of the drop-out layer. The difference metric may include, or be based on, e.g. a standard deviation or variance for any or each of the parameters in the set of parameters and/or the like.

Larger standard deviations, for example, indicate larger difference between the individual parameters 73 and thus indicate that the at least one parameter 73 is comparatively dependent on individual nodes of the artificial neural network, ANN, 55 and is thus comparatively less reliable.

The determined reliability metric 74 may then be output via the output interface 90 together with the generated at least one parameter 73.

The system 100 may further include a user interface 60, for example a touch-screen interface implementing a graphical user interface, a computer monitor in combination with a keyboard and/or a mouse, a speech-controlled user interface and/or the like. The user interface 60 may be configured to obtain, at least in a revision mode of the system, revision information by a user. The user may put the system 100 into the revision mode or the system 100 may permanently be in the revision mode. The revision information indicates a resonance frequency spectrum, RFS, 71 for which the trained machine learning algorithm, MLA, 55 has generated the at least one parameter 73 as well as indicate a confirmation of at least one parameter of the generated at least one parameter 73 and/or a correction to at least one parameter of the generated at least one parameter 73. The revision information may include a confirmation or correction of the generated water resonance frequency value.

For example, in the revision mode, after the at least one parameter 73 has been generated, it may be visually displayed to a user by the user interface 60 together with the underlying resonance frequency spectrum, RFS, 71, and the user may be prompted to confirm or correct a single one (preferably the water resonance frequency value) or each of the parameters of the at least one parameter 73. The generated at least one parameter 73 may be automatically visually indicated within the resonance frequency spectrum, RFS, 71, so that the user may immediately verify if the generated at least one parameter is accurate and/or acceptable. The user interface 60 may provide the user with the option to shift and/or move graphical indications of the generated at least one parameter 73 within the visual display of the underlying resonance frequency spectrum, RFS, 71. When the user does so, the at least one parameter 73 may be concurrently modified/corrected according to the settings made by the user.

If the reliability metric 74 has been calculated, it may be automatically displayed by the user interface 60 as well to indicate to the user how important the user's revision of the generated at least one parameter 73 (for example, the water resonance frequency value) is. Alternatively, the system may normally not be in the revision mode and may be put into the revision mode automatically if and only if the reliability metric 74 is below a predefined threshold, i.e. when the reliability of the generated at least one parameter 73 has been determined to be low. Thus, as long as the reliability metric 74 is determined to be high compared to the predefined threshold, the at least one generated parameter 73 may be automatically forwarded for further processing, e.g. for controlling an MR scanning device. If and when, however, the reliability metric 74 is determined to be low compared to the predefined threshold, user revision is required for either correcting and/or confirming each parameter or at least specifically indicated parameters (e.g. in case that the reliability metric 74 indicates particular parameters to be particularly unreliable).

The finally confirmed/corrected parameter set may automatically be transmitted to a training entity, for example for additional training of the machine learning algorithm, MLA.

Figure 2:
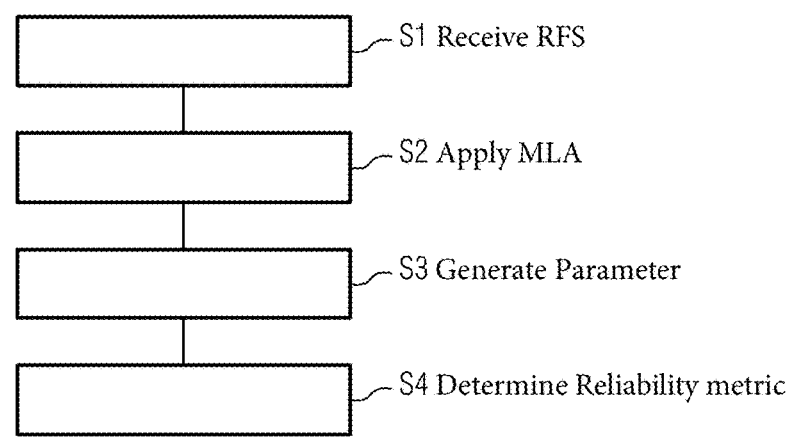
FIG. 2 depicts a schematic flow diagram illustrating a computer-implemented method according to an embodiment.

FIG. 2 depicts a schematic flow diagram schematically depicting a computer-implemented method for providing at least one parameter (in particular a water resonance frequency value) of a resonance frequency spectrum, RFS, of a magnetic resonance, MR, scan according to an embodiment. The method may be performed using the system according to any embodiment, for example, the system 100 as has been described with respect to FIG. 1. The method may also be performed independently from the system 100 or systems.

In a step S1, a resonance frequency spectrum, RFS, 71 of a magnetic resonance, MR, scan is received, for example by the input interface 10 of the system 100. As has been described in the foregoing, also additional pieces of information may be received such as additional pieces of patient information 72, including information about the weight of the patient, a height of the patient, a body region of the patient from which the resonance frequency spectrum, RFS, 71 has been taken and/or patient identifier information.

In a step S2, a trained machine learning algorithm, MLA, 55 is applied to the received resonance frequency spectrum, RFS, 71. As the output of the machine learning algorithm, MLA, 55 at least one parameter 73 of the resonance frequency spectrum, RFS, is generated. The at least one parameter 73 includes at least the water resonance frequency value. The other content and/or properties of the at least one parameter 73 may vary as has been described in the foregoing. In certain embodiments, the at least one parameter includes position (or: location), FWHM, and height of the local maxima within the fitting curve to the resonance frequency spectrum, RFS, 71 corresponding to fat and water, and the local maximum corresponding to silicon.

The machine learning algorithm, MLA, 55 may be a trained artificial neural network, ANN. The artificial neural network, ANN, may be a feed-forward artificial neural network trained with resonance frequency spectra, RFS, 71 as training input, that are labeled with the corresponding at least one parameter as ground truth. The trained artificial neural network, ANN, 55 is configured to generate, from resonance frequency spectra, RFS, 71 as its input the desired at least one parameter 73 as its output.

In addition to the resonance frequency spectrum, RFS, 71 in step S1 additional pieces of patient information 72 may be received. If the machine learning algorithm, MLA, 55 for example, the artificial neural network, ANN, 55 is configured accordingly, at least one or all of the received pieces of patient information 72 are input into the artificial neural network, ANN, 55 alongside the resonance frequency spectrum, RFS, 71 to improve the accuracy and precision of the generated at least one parameter 73.

In case that a specific piece of patient information is missing, a step of requesting the piece of patient information may be performed to receive S1 the corresponding piece of patient information from an external source. The request may be output in a dialog field of a graphical user interface to a user such as a physician that may then enter the desired piece of patient information manually.

The resonance frequency spectrum, RFS, of the magnetic resonance, MR, scan may be received directly from an MR scanning device. In some cases, the system 100 is integrated into an MR scanning device itself. The MR scanning device may first measure the resonance frequency spectrum, RFS, provide it to the system 100 via the input interface 10 and receive, via the output interface 90 of the system 100, the generated at least one parameter 73. Then, the MR scanning device may be configured to automatically perform an MR scan based on the received at least one parameter 73.

In a revision mode, that may be a standard mode or a mode only set upon explicit to request by a user, a user of the MR scanning device may be prompted to confirm and/or correct any or each of the parameter(s) of the at least one parameter 73 generated by the system 100. In the revision mode, only when each parameter (for which confirmation/correction has been prompted to the user) of the at least one 73 of parameters has been either confirmed or corrected, is the (possibly corrected/updated) at least one parameter forwarded to the rest of the MR scanning device for use within an MR scan.

In a step S3, the at least one parameter 73 generated by the trained machine learning algorithm, MLA, is output, for example by the output interface 90 of the system 100. In case that the system 100 is integrated into an MR scanning device, the input interface 10 and the output interface 90 may be internal interfaces within the MR scanning device itself. The input interface 10 and the output interface 90 may even be solely configured as software interfaces, for example, when the MR scanning device includes a single computing device 50, that is, among others, used to implement the trained machine learning algorithm, MLA 55. The system 100 may also implement other modules, for example an MR scan control module, that requires the generated at least one parameter 73 for its accurate operation. The input interface 10 and the output interface 90 may in that case be software interfaces between the machine learning algorithm module 56 implemented by the computing device 50 and the MR scan control module also implemented by the computing device 50.

In a step S4, a reliability metric 74 is determined and is output together with the generated at least one parameter 73.

Figure 3:
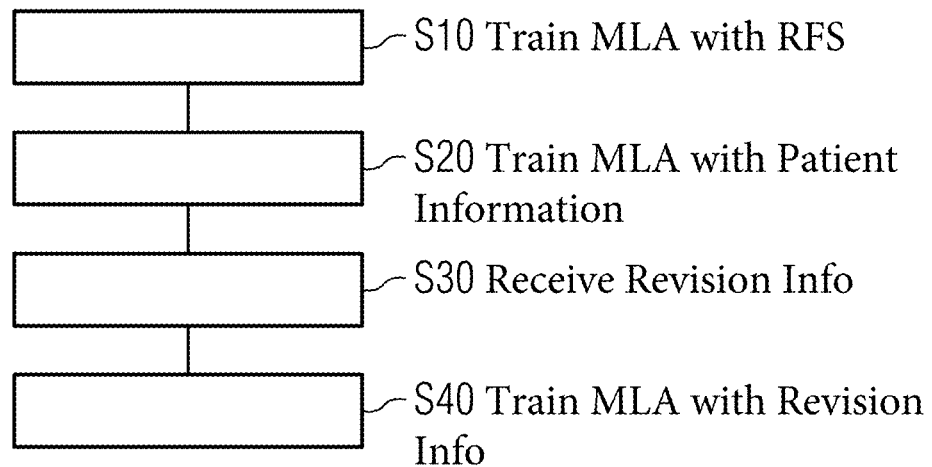
FIG. 3 depicts a schematic flow diagram illustrating a computer-implemented method according to an embodiment.

FIG. 3 depicts a flow diagram schematically illustrating a computer-implemented method for training a machine learning algorithm, MLA, 55 for example an artificial neural network, ANN, for use in a method or a system for providing at least one parameter of a resonance frequency spectrum, RFS, 71 of a magnetic resonance, MR, scan, for example, for providing a water resonance frequency value. The method depicted with respect to FIG. 3 may be used for training a machine learning algorithm, MLA, 55 for use in a system 100 of FIG. 1 and/or for use with the method described with respect to FIG. 2.

In a first step S10, the machine learning algorithm, MLA, 55 is trained with labeled resonance frequency spectra, RFS 71. The resonance frequency spectra, RFS, 71 may be labeled with the correct at least one parameter that is/are to be generated based on the resonance frequency spectrum, RFS, 71.

In a step S20, the machine learning algorithm is additionally and simultaneously with step S10 trained with, as additional input, at least one piece of patient information 72 about each of the patients from which the labeled resonance frequency spectra, RFS, 71 were taken. For example, each training sample for the machine learning algorithm, MLA, 55 may include a resonance frequency spectrum, RFS, 71 and at least one piece of patient information 72 (for example weight, height, or body region of the patient), together with the labels indicating the at least one parameter 73 is correct for the particular resonance frequency spectrum, RFS.

The training samples may include, apart from the resonance frequency spectrum, RFS, 71 pieces of information about each of the weight of the patient, the height of the patient, and the body region of the patient (and additional pieces of information such as an age of the patient, a gender of the patient and/or the like). Comparatively easy to procure pieces of information may be used to improve the quality of the training of the machine learning algorithm, MLA that may improve, for example, the capability of the machine learning algorithm, MLA, 55 to learn, during training, possibly hidden correlations and connections and so to generate better, more accurate and more precise parameters 73.

Whenever users confirm and/or correct parameters 73 generated by the trained machine learning algorithm, MLA, during the inference phase, the corrected and/or confirmed parameters 73 may be transmitted, together with the corresponding (or, in other words: underlying) resonance frequency spectrum, RFS, to a training entity.

In a step S30, the revision information may be received by the training entity.

In a step S40, the training entity may further train the machine learning algorithm, MLA, previously pre-trained in steps S10 and S20, based on the received S30 revision information, i.e. the resonance frequency spectra, RFS, 71 input in the inference phase together with their corrected/confirmed parameters 73. If the machine learning algorithm is configured to receive, as its input, at least one additional piece of patient information, the revision information also includes this at least one piece of patient information for the training entity.

The training entity may be a computer program configured to further train the machine learning algorithm, MLA, based on the revision information. Embodiments provide a training entity for performing the method according to any embodiment, for example, the method of FIG. 3.

Figure 4:
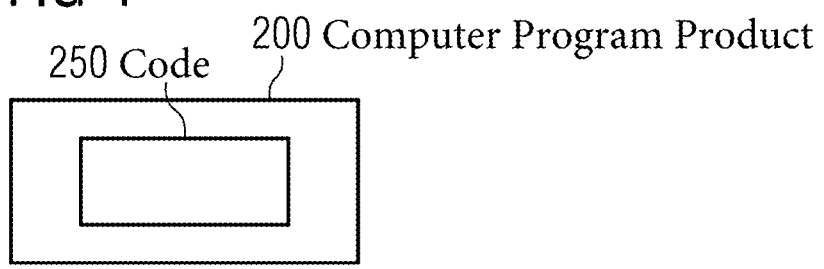
FIG. 4 depicts a schematic block diagram illustrating a computer program product according to an embodiment.

FIG. 4 depicts a schematic block diagram depicting a computer program product 200 according to an embodiment. The computer program product 200 includes executable program code 250 configured to, when executed by a computing device (e. g. computing device 50 of system 100), to perform the method according to FIG. 2. Alternatively, or additionally, the computer program product 200 may include executable program code 250 configured to, when executed by a computing device (e. g. computing device 50 of system 100), to perform the method according to FIG. 3.

Figure 5:
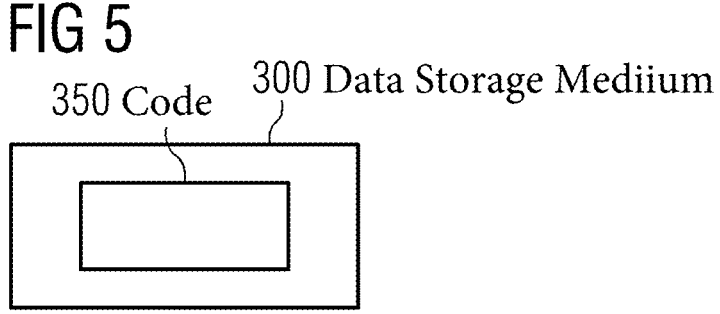
FIG. 5 depicts a schematic block diagram illustrating a data storage medium according to an embodiment.
Figure 6:
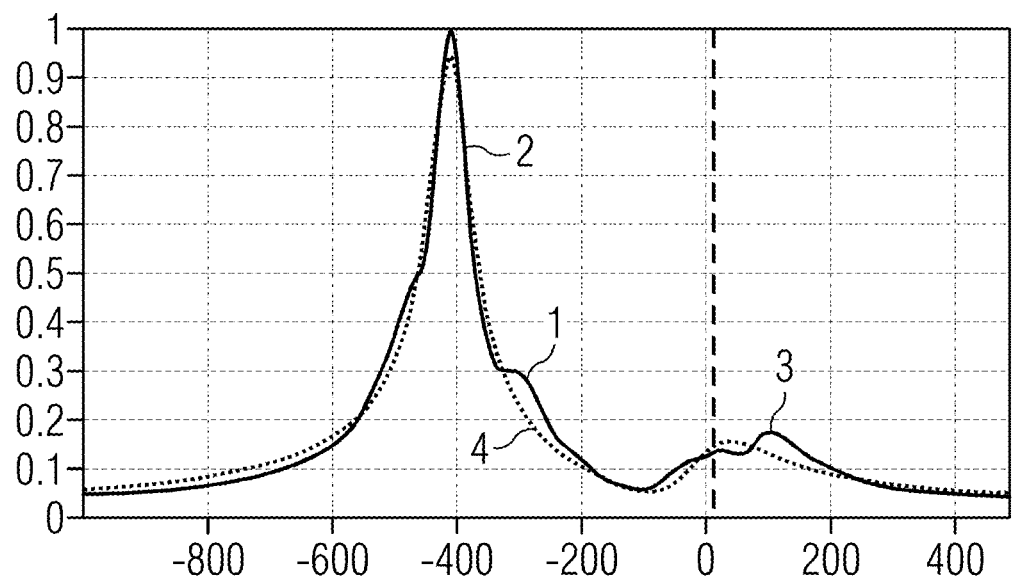
FIG. 6 illustrates typical resonance frequency spectra and the problems associated with the prior art.
Figure 7:
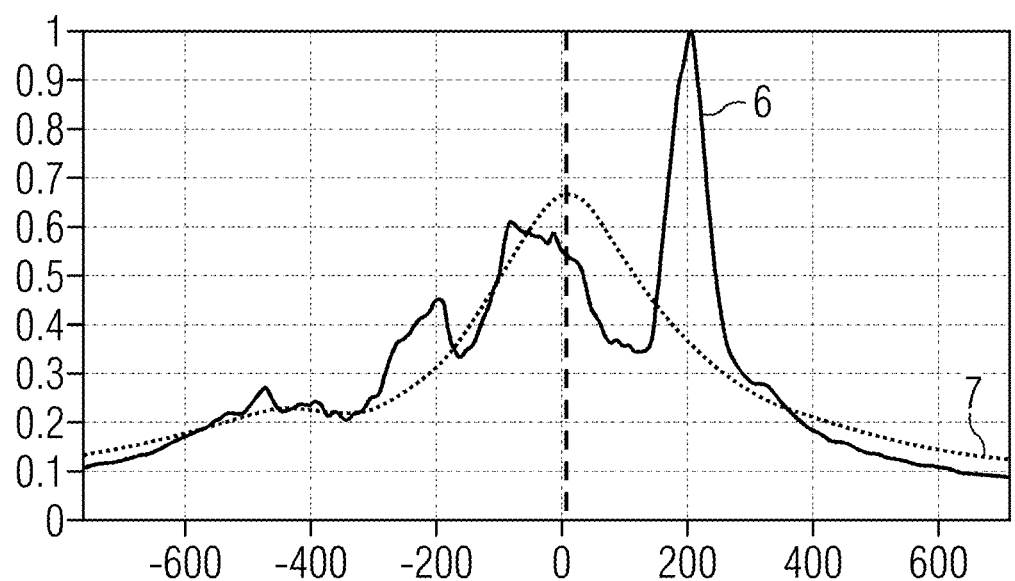
FIG. 7 illustrates typical resonance frequency spectra and the problems associated with the prior art.

FIG. 5 depicts a schematic block diagram illustrating a non-transitory, computer-readable data storage medium 300 including executable program code 350 configured to, when executed by a computing device (such as computing device 50 of system 100), to perform the method according to FIG. 2. Alternatively, or additionally, the data storage medium 300 may include executable program code 350 configured to, when executed by a computing device (e. g. computing device 50 of system 100), to perform the method according to FIG. 3.

In the foregoing detailed description, various features are grouped together in the examples with the purpose of streamlining the disclosure. It is to be understood that the above description is intended to be illustrative and not restrictive. It is intended to cover all alternatives, modifications, and equivalence. Many other examples will be apparent to one skilled in the art upon reviewing the above specification, taking into account the various variations, modifications, and options as described or suggested in the foregoing.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A system for providing at least one parameter for a magnetic resonance scan, the system comprising:
    an input interface configured to receive a resonance frequency spectrum of the magnetic resonance scan;
    a computing device configured to implement a trained machine learning algorithm, wherein the trained machine learning algorithm is trained to input the resonance frequency spectrum and generate the at least one parameter comprising at least a water resonance frequency value; and
    an output interface configured to output at least the water resonance frequency value.

2. The system of claim 1, wherein the at least one parameter further includes, for at least one local maximum of a fitting curve to the resonance frequency spectrum, at least one of a position of a local maximum, a full width at half maximum of the local maximum, or a height of the local maximum.

3. The system of claim 2, wherein the at least one parameter indicates, for the at least one local maximum of the fitting curve to the resonance frequency spectrum, to which type of substance or tissue the at least one maximum corresponds.

4. The system of claim 3, wherein the at least one parameter indicates for at least one of water, fat, or silicon a corresponding local maximum of the fitting curve to the resonance frequency spectrum.

5. The system of claim 1, wherein the trained machine learning algorithm is a feed-forward artificial neural network.

6. The system of claim 1, further comprising a user interface configured to obtain, at least in a revision mode, revision information by a user, wherein the revision information indicates an resonance frequency spectrum for which the trained machine learning algorithm has generated the at least one parameter and indicates a confirmation of at least one parameter of the generated at least one parameter, a correction to at least one parameter of the generated at least one parameter, or the confirmation and the correction.

7. The system of claim 1, wherein the trained machine learning algorithm further receives as its input, together with the resonance frequency spectrum, at least one piece of patient information about a patient from which the resonance frequency spectrum was taken.

8. The system of claim 7, wherein the at least one piece of patient information comprises information about at least one of: a weight of the patient, a height of the patient, an age of the patient, a sex of the patient, or a body region of the patient from which the resonance frequency spectrum was taken.

9. The system of claim 1, wherein the trained machine learning algorithm comprises at least one dropout layer, wherein the computing device is further configured to determine a reliability metric of the generated set of parameters based on at least one configuration of the at least one dropout layer; and wherein the output interface is further configured to output the determined reliability metric.

10. A computer-implemented method for providing at least one parameter for a magnetic resonance scan, the method comprising:
    receiving a resonance frequency spectrum of the magnetic resonance scan;
    applying a trained machine learning algorithm to the received resonance frequency spectrum, the trained machine learning algorithm configured to output the at least one parameter comprising at least a water resonance frequency value when input the resonance frequency spectrum; and
    outputting at least the water resonance frequency value generated by the trained machine learning algorithm.

11. The computer-implemented method of claim 10, wherein the trained machine learning algorithm is trained with labelled resonance frequency spectrums.

12. The computer-implemented method of claim 11, wherein the trained machine learning algorithm is additionally trained with the at least one piece of patient information about each patient of a plurality of patients from which the labelled resonance frequency spectrums were taken.

13. The computer-implemented method of claim 10, wherein the trained machine learning algorithm is further trained using received revision information.

14. A non-transitory computer-readable data storage medium that stores machine-readable instructions executable by at least one processor for providing at least one parameter for a magnetic resonance scan, the machine-readable instructions comprising:
    receiving a resonance frequency spectrum of the magnetic resonance scan;
    applying a trained machine learning algorithm to the received resonance frequency spectrum, the trained machine learning algorithm configured to output the at least one parameter comprising at least a water resonance frequency value when input the resonance frequency spectrum; and
    outputting at least the water resonance frequency value generated by the trained machine learning algorithm.

15. The non-transitory computer-readable storage medium of claim 14, wherein the trained machine learning algorithm is trained with labelled resonance frequency spectrums.

16. The non-transitory computer-readable storage medium of claim 14, wherein the at least one parameter further includes, for at least one local maximum of a fitting curve to the resonance frequency spectrum at least one of a position of a local maximum, a full width at half maximum of the local maximum, or a height of the local maximum.

17. The non-transitory computer-readable storage medium of claim 16, wherein the at least one parameter indicates, for the at least one local maximum of the fitting curve to the resonance frequency spectrum, to which type of substance or tissue the at least one maximum corresponds.

18. The non-transitory computer-readable storage medium of claim 17, wherein the at least one parameter indicates for at least one of water, fat, or silicon a corresponding local maximum of the fitting curve to the resonance frequency spectrum.

19. The non-transitory computer-readable storage medium of claim 14, wherein the trained machine learning algorithm further receives as its input, together with the resonance frequency spectrum, at least one piece of patient information about a patient from which the resonance frequency spectrum was taken.

20. The non-transitory computer-readable storage medium of claim 19, wherein the at least one piece of patient information comprises information about at least one of: a weight of the patient, a height of the patient, an age of the patient, a sex of the patient, or a body region of the patient from which the resonance frequency spectrum was taken.

\* \* \* \* \*